United States Patent
Steel et al.

(10) Patent No.: US 6,224,853 B1
(45) Date of Patent: May 1, 2001

(54) AQUEOUS COMPOSITIONS COMPRISING A LIPID AND A LANOLIN-DERIVED SURFACTANT, AND THEIR USE

(75) Inventors: Ian Steel, Leeds; Guy Stanley Hawksworth Kitchen, Bingley; Ian Ronald Flockhart, Little Weighton, all of (GB)

(73) Assignee: Woolcombers Group PLC, Bradford (GB)

( * ) Notice: Subject to any disclaimer, the term of this patent is extended or adjusted under 35 U.S.C. 154(b) by 0 days.

(21) Appl. No.: 09/403,526

(22) PCT Filed: Apr. 22, 1998

(86) PCT No.: PCT/GB98/01174

§ 371 Date: Feb. 1, 2000

§ 102(e) Date: Feb. 1, 2000

(87) PCT Pub. No.: WO98/47468

PCT Pub. Date: Oct. 29, 1998

(30) Foreign Application Priority Data

Apr. 22, 1997 (GB) .................................................... 9708066

(51) Int. Cl.⁷ .............................. A61K 31/74; A61K 7/42
(52) U.S. Cl. ..................... 424/59; 424/78.02; 424/78.03
(58) Field of Search ............................. 424/78.02, 78.03, 424/59

(56) References Cited

U.S. PATENT DOCUMENTS

| | | | |
|---|---|---|---|
| 3,666,857 | * 5/1972 | Russel | 424/240 |
| 4,254,104 | 3/1981 | Suzuki | 424/170 |
| 5,154,854 | * 10/1992 | Zabotto et al. | 252/312 |
| 5,439,672 | * 8/1995 | Zabotto et al. | 424/59 |
| 5,489,426 | * 2/1996 | Zabotto et al. | 424/59 |

FOREIGN PATENT DOCUMENTS

| | | |
|---|---|---|
| 0 349 150 | 1/1990 | (EP) . |
| 0399843 | * 11/1990 | (EP) . |
| 0 399 843 | 11/1990 | (EP) . |
| 2 297 762 | 8/1996 | (GB) . |
| 66678 | * 1/1979 | (RO) . |

OTHER PUBLICATIONS

Flokhart I.R. et al. "Nanoemulsions derived from Ian . . . " J.Pharm.Pharmacol.50, 141, Jan. 1998.*

* cited by examiner

Primary Examiner—Mukund J. Shah
Assistant Examiner—Sudhaker B. Patel
(74) Attorney, Agent, or Firm—Cantor Colburn LLP

(57) ABSTRACT

An aqueous composition comprising, in addition to water: (a) one or more surfactant materials selected from polyoxyalkylene condensate derivatives of lanolin or a lanolin derivative; and (b) a lipid component comprising one or more lipid materials, especially lanolin or a lanolin derivative, present as particles emulsified by the said one or more lanolin-derived surfactant materials and having a median particle size of less than about 5 $\mu$m, especially from 0.01 to 1 $\mu$m. The compositions have very good physical stability and are particularly useful as carriers for transdermal delivery of pharmaceutical actives to the human skin.

15 Claims, No Drawings

AQUEOUS COMPOSITIONS COMPRISING A LIPID AND A LANOLIN-DERIVED SURFACTANT, AND THEIR USE

FIELD OF THE INVENTION

This invention relates to aqueous compositions containing lipid materials such as lanolin or lanolin derivatives, more particularly to such compositions in which the lanolin or lanolin derivative (or other lipid material) is present in the form of very small emulsified particles. The invention further relates to the use of these compositions for treating parts of the mammalian body, particularly the skin, and especially for use as carriers for the delivery of active agents, e.g. pharmaceuticals.

BACKGROUND OF THE INVENTION AND PRIOR ART

Lanolin and certain lanolin derivatives, as examples of lipid materials, are well known for their unique blend of emollient, moisture retentive and skin penetrating properties, particularly in compositions such as cosmetics and medicaments for treatment of the skin and other parts of the body. The chemical constitution of lanolin and its useful properties are discussed for example in European Patent Application EP-A-0602961. Examples of lanolin-containing compositions in the form of oil-in-water emulsions for cosmetic and other applications are disclosed for instance in GB-A-1530064 and U.S. Pat. No. 3,666,857.

Lanolin has also been used historically as a secondary emulsifier in cosmetic products, imparting an improved skin feel to both vegetable oil and petrolatum based systems. However, because of limitations caused by the drag tackiness and odour of unmodified lanolin on its own, its full range of moisturising and other properties has hitherto been little exploited.

In an article by Clark, E.W., Manufacturing Chemist, 1990, 61, 18–23, it is disclosed that lanolin penetrates into mammalian stratum corneum and also emulsifies water at the lanolin/water interface to give a localised water-in-oil emulsion exhibiting a very small droplet size of less than about 6 $\mu$m. Thus, the moisturising effects of lanolin within the stratum corneum may be in part due to this ability to form a spontaneous microemulsion. Further evidence of this effect is disclosed in a later article by Clark, E.W., and Steel, I, J. Soc. Cosmet. Chem., 1993, 44, 181–195.

The scientific literature contains several other reports concerning the ability of lanolin, or modified derivatives of lanolin, either alone or in combination with film-forming agents, to act as enhancers of drug release from matrices. Relevant references in this regard include: R. I Ellin, P.J. Levine and D.E. Leco, J. Am. Pharm. Assoc. 1955, 16, 747–749, L. von Sallman, A.E. Grosso, and M.G Marsh, Arch. Opthalmol., 1946, 36, 284–292 and F. Bottari, 20 G. Di Colo, E. Nannipieri, M.F Saettone and M.F. Serafini, J. Pharm. Sci., 1974, 63, 1779–1783.

In the broader field of micellar dispersion technology, it is well known and well documented that stable compositions having useful carrier and penetration properties can be prepared based on the formation of so-called liposomes, which can approximately be defined as aqueous dispersions of particles which are themselves made up of one or several concentric lipid bilayers within which other molecules can be incorporated. GB-A-1539625 and GB-A-2013609 for example disclose stabilised liposome-based dispersions, in which the liposomal spherules are capable of encapsulating various active substances. Various ionic or nonionic lipid compounds are disclosed, the preferred being a nonionic lipid compound selected from certain linear or branched polyglycerol ethers, polyoxyethyleneated fatty alcohols, various polyol esters or natural or synthetic glycolipids.

EP-A-0585157 and published International patent application WO 87/06499 both disclose the formation of liposome-like particles which incorporate long chain alcohols, some of which are known to be provided by lanolin alcohols, and which are stabilised by the necessary presence of cholesterol or cholesterol sulphate salts. However, we have discovered that the stabilising effect claimed for cholesterol and its sulphate salts is not an essential requirement and that simple microemulsions or liposome-like structures exhibiting excellent physical stability can be produced using lanolin-based materials with a particularly small particle size, the compositions produced being low in viscosity and not necessitating the inclusion of stabilisers or auxiliary emulsifiers.

SUMMARY OF THE INVENTION

Accordingly, and in accordance with the present invention, the advantages of microemulsion and/or liposome technology and the benefits exhibited by lanolin and lanolin derivatives as exemplary lipid materials may be combined by the provision, according to a first aspect of the invention, of an aqueous composition comprising, in addition to water:

(a) one or more surfactant materials selected from polyoxyalkylene condensate derivatives of lanolin or a lanolin derivative; and (b) a lipid component comprising one or more lipid materials present as particles emulsified by the said one or more lanolin-derived surfactant materials and having a median particle size of less than about 5 $\mu$m.

DETAILED DESCRIPTION OF THE INVENTION AND PREFERRED EMBODIMENTS

The emulsion-based compositions of the invention are characterised not only by the extremely small median particle size of the dispersed lipid phase of less than about 5 $\mu$m, but also, in the most preferred embodiments of the invention, by a hitherto unknown combination of particularly high solids content and low viscosity. Many of the compositions according to the invention, in particular those with median particle sizes of the lipid component from about 5 $\mu$m down to around 0.1 $\mu$m, may have a milky appearance. The compositions of the invention are furthermore physically very stable upon storage.

In the compositions of the present invention the lipid component comprises one or more lipid materials present as emulsified particles having the defined very small particle size. Various known lipid materials may be suitable for use in the invention, either singly or as mixtures of two or more such lipid materials.

In preferred embodiments of the compositions of the invention the lipid component comprises lanolin or one or more lanolin derivatives which typically exhibit at least some of the same advantageous properties of lanolin itself. Wool wax or purified lanolin (lanolin purified to varying levels of removed impurities such as allergens and pesticides) may be used as a lanolin per se lipid component. Such lanolin for use in the invention may be hydrous or, more preferably, anhydrous. Physically or chemically obtained lanolin derivatives suitable for use as a lanolin-derived lipid component may include for example lanolin oil, lanolin alcohols and lanolin esters (e.g. isopropyl lanolate). Suitable examples of these lanolin and lanolin-derived materials are readily available commercially and their derivation and/or preparation is widely documented in the patent and technical literature.

Other lipid materials which may be suitable for use as or in the lipid component of the compositions of the invention include the following:

(i) waxes, e.g. esters of monohydric alcohols of the higher homologues;

(ii) long chain hydrocarbons, e.g. $C_{12}$ to $C_{60}$ hydrocarbons;

(iii) fats, in particular glycerides (e.g. mono-, di-, or triglycerides) of higher fatty acids;

(iv) oils, such as:
  (a) fatty oils derived from animal, vegetable or marine sources, e.g. mono-, di-, or triglycerides of fatty acids;
  (b) mineral oils, e.g. non-volatile hydrocarbons;
  (c) essential oils, e.g. plant-derived volatile or non-volatile oils;

(v) neutral glycerolipids, e.g. mono-, di-, and tri- acylglycerols and their neutral derivatives (e.g. alkoxy and polyalkoxy derivatives), acyl derivatives of glycerophospholipids and mono- and di- galactoacylglycerols;

(vi) polar lipids, e.g. glycerophospholipids, sphingomyelins, galactosylacylglycerols;

(vii) phospholipids;

(viii) terpenes;

(ix) sterols;

(x) ceramides.

In the compositions of the invention the lipid component is present as particles emulsified by the one or more lanolin-derived surfactant materials and having a median particle size of less than about 5 $\mu$m, more preferably less than about 2 or 3 $\mu$m, even more preferably less than about 1 $\mu$m. The term "emulsified" is to be construed here not necessarily in the strict sense of classical emulsion technology, where discrete particles or droplets of the lipid component are dispersed in the continuous aqueous phase, but rather it should be construed as encompassing the lipid component being present in the form of so-called micro- or nano-particles, Aphrons or even liposome-type structures comprising uni- or multi-laminar micellar dispersed particles or droplets. In accordance with the invention, however, it is the lanolin-derived surfactant material (s) which emulsify and stabilize the lipid-containing particles in the composition.

In especially preferred embodiments of the composition of the invention the median particle size of the lipid component is preferably in the range of from about 0.01 up to about 1 $\mu$m, more preferably from about 0.02 up to about 0.8 or 0.9 $\mu$m. The range of actual particle sizes of the dispersed droplets may typically be within these preferred ranges, although the distribution may be such as to include some particles having sizes outside these ranges, as is typical in particle size distribution patterns of microemulsion systems known in the art. In the context of the invention particle sizes can be readily measured by techniques well known in the art, e.g. using a Malvern Mastersizer instrument.

The compositions of the invention typically have relatively low kinematic viscosities, preferably in the range of from about 1.5 to about 20 mm$^2$sec$^{-1}$, more preferably from about 1.5 to about 10 mm$^2$sec$^{-1}$ at 21° C. Kinematic viscosities are readily measured for instance using a glass U-tube viscometer as described in the British Pharmacopoeia, 1993 Edition (Appendix VII Method 1, carried out in accordance with ISO 3104, 1976).

The amount of the lipid component in the compositions of the invention is preferably from about 0.1 to about 60% by weight, more preferably from about 1 to about 30% by weight of the total composition. The exact amount may be selected according to for instance the intended use of the composition and the property or properties, especially the lanolin-derived properties where the lipid component comprises lanolin or a lanolin derivative, to be delivered by it.

In the compositions of the invention the primary surfactant comprises the one or more surfactant materials which are selected from polyoxyalkylene condensate derivatives of lanolin or a lanolin derivative. In this context, suitable lanolin derivatives comprise those defined above with respect to the preferred lanolin-based lipid component of the composition.

Suitable polyoxyalkylene condensate derivatives of lanolin or a lanolin derivative for use as the primary surfactant in the compositions of the invention are derived from lanolin or the relevant lanolin derivative by condensation with an appropriate number of alkoxy (especially ethoxy) groups, techniques for which are well known in the art of conventional alkoxylated surfactants. Examples of these surface-active polyoxyalkylene lanolin derivatives which may be suitable for use in the invention include any of the following, either singly or in any combination: 20 mol polyethyleneglycol ether of lanolin alcohol, which has the CTFA adopted name LANETH-20, available as AQUALOSE W20 (trade mark); 5 mol polypropyleneglycol ether of lanolin alcohol (CTFA adopted name: PPG-5 LANOLIN ETHER), available as AQUALOSE LW5 (trade mark); 30 mol and 75 mol polyethyleneglycol ethers of lanolin (CTFA adopted names, respectively: PEG-30 LANOLIN and PEG-75 LANOLIN), available respectively as AQUALOSE L30 and L75 (trade marks); and 40 mol PPG/60 mol PEG ether of lanolin oil (CTFA adopted name: PPG-40-PEG 60 LANOLIN OIL), available as AQUALOSE LL100 (trade mark); all from Westbrook Lanolin Company.

The compositions of the invention may optionally additionally contain one or more co-surfactant materials, which may be selected from various natural, synthetic or semi-synthetic surface active substances capable of forming in the aqueous phase a matrix structure within which the other ingredients are dispersed. Such co-surfactants may serve as additional emulsifying agents for the lipid component and/or may be useful to adjust the overall physical properties of the compositions, e.g. in order to optionally suit particular end-uses.

Suitable naturally-derived co-surfactant materials which act as matrix- or film-formers include those based on cellulose (e.g. methylcellulose, carboxymethylcellulose), alginate (e.g. sodium alginate) or chitosan.

Suitable synthetic co-surfactant materials may be selected from a wide variety of known surfactants chosen from anionic, nonionic, cationic, zwitterionic or amphoteric surfactants, or mixtures thereof.

Suitable anionic co-surfactants are the alkyl sulphates, alkyl ether sulphates, alkaryl sulphonates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule, and preferably contain 2 to 3 ethylene oxide units per molecule.

Examples of suitable anionic co-surfactants include sodium oleyl succinate, ammonium lauryl sulphosuccinate, ammonium lauryl sulphate, sodium dodecylbenzene sulphonate, triethanolamine dodecylbenzene sulphonate, sodium N-lauryl sarcosinate, sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

The nonionic co-surfactants suitable for use in compositions of the invention may include condensation products of aliphatic ($C_8$–$C_{18}$) primary or secondary linear or branched chain alcohols or phenols with alkylene oxides, usually ethylene oxide and generally 6–30 EO.

Other suitable nonionics include mono- or di- alkyl alkanolamides or alkyl polyglucosides. Examples include coco-mono- or diethanolamide, coco-mono-isopropanolamide, and coco-di-glucoside.

The amphoteric co-surfactants suitable for use in compositions of the invention may include alkyl amine oxides, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to 18 carbon atoms. Examples include lauryl amine oxide, cocodimethyl sulphopropyl betaine and preferably lauryl betaine, cocamidopropyl betaine and sodium cocamphopropionate.

Further examples of suitable co-surfactants for use in compositions of the invention include surface-active phospholipids (e.g. lecithin) or surfactants which are polyoxyalkylene condensate derivatives of sterols.

In preferred compositions of the invention the surfactant component consists substantially only of the one or more polyoxyalkylene condensate derivative(s) of lanolin or a derivative thereof, with other surfactant (i.e. co-surfactant) materials being substantially absent.

The total amount of surfactant in the compositions of the invention is preferably in the range of from about 0.1 to about 25% by weight, more preferably from about 0.1 to about 10% by weight, even more preferably from about 1.0 to 10% by weight of the total composition.

The aqueous continuous phase of the compositions of the invention may comprise purified (e.g. deionised) water, or alternatively saline or buffer solution, whichever is most appropriate to the form and intended use of the composition. Typically the aqueous phase provides the balance by weight to 100% of the total composition and may include one or more conventional buffering agents in order to maintain a pH value of the composition in the range of about 3.5 to about 8.5.

Various additional components may optionally be included in the compositions of the invention in order to confer additional desirable properties or to modify existing properties. Such adjunct ingredients may typically include any of the following: polymers such as carboxylic acid copolymers (e.g. of the Carbomer type), silicones, inorganic materials such as clays (e.g. Bentonite), silica or inorganic salts (e.g. aluminium trichloride), and viscosity-adjusting agents. These adjunct materials may be included in order to confer desirable properties on the composition such as ease of application, skin feel, consistency, optimum viscosity, reduced drag, tack, odour, rub out, but will normally be selected and added in such an amount so as not to affect the general desirable properties of the composition itself. Suitable amounts of such adjunct materials will be readily apparent to the person skilled in the art on the basis of conventional knowledge.

The compositions of the invention furthermore preferably include a suitable preservative and/or antioxidant system, examples of which are well known in the art and widely available commercially.

In accordance with a second aspect of the present invention, the compositions of the first aspect are prepared by a process which involves forming a mixture of the components of the composition, and processing the mixture using high intensity (e.g. high shear) emulsifying apparatus, in order to obtain the extremely small particle size of the lipid component. Any suitable high intensity (e.g. high shear) emulsifying equipment may be used, for example a Microfluidics Microfluidiser, or other machine capable (e.g. by virtue of settings of pressure (e.g. from about 5,000 to about 25,000 or 30,000 psi, more preferably from about 10,000 to about 20,000 psi) and/or temperature (e.g. from about room temperature up to about 100° C., more preferably from about 40 to about 70° C.) and/or number of passes therethrough e.g. at least 1 or 2 passes) of reducing the median particle size to less than 5 $\mu$m, most preferably to less than 1 $\mu$m. Other suitable emulsifying techniques may for instance include ultrasonic agitation or Nucleopore (trade mark) membrane filtration.

For use, the compositions of the invention may be formulated or presented in any suitable form according to the intended use. Thus, suitable delivery forms may include sprays, aerosols, lotions, bath dispersions, shampoos, drenches, ointments, creams, gels, salves, patches, pessaries, suppositories or any other suitable dosage form such as is typically used for the delivery of cosmetically or pharmacologically active agents.

Because of the lanolin or lanolin derivative content of the compositions according to preferred embodiments of the invention, they find particularly useful utility in the treatment of parts of the mammalian body, especially topical application to the skin, for various purposes.

For example, the compositions of the invention may be used as skin moisturisers or for the provision of a film or barrier to allow both the delivery of medicaments to underlying traumatised skin (e.g. to wounds, burns, ulcers) or to eczematous or psoriatic skin or to areas of generalised dry or damaged skin or hair, e.g. following excessive exposure to sun or wind or after radiation or chemotherapy treatments, and also to prevent the actions of airborne infections to such aforesaid traumas.

Other embodiments of the invention in which the lipid component comprises lipid material(s) other than lanolin or a lanolin derivative may find other desirable uses, for example dependent on the lipid material(s) in question.

Compositions according to the invention may also be useful in agricultural or industrial applications, e.g. in the delivery of pesticides to crops or to replace conventional uses of mineral oil, e.g. as cutting fluids.

According to a third aspect of the present invention, the compositions of the first aspect of the invention constitute carriers for one or more cosmetic or pharmaceutical active agents which are incorporated into the compositions so that they may be efficiently delivered to the skin, mucosae or other parts of the body by application of the composition thereto.

In accordance with this aspect of the invention, a wide range of cosmetically, dermatologically and/or pharmaceutically active agents may be incorporated into the compositions of the invention, examples of which are well known in the art. A wide variety of suitable such bio-affecting active agents are disclosed for example in U.S. Pat. No. 4,560,553. The amount of active which is incorporated may be selected according to the amount required to be delivered, which again will generally be in accordance with well established principles and formulation techniques. The use of the compositions of the invention as vehicles for transdermally delivered drugs in pharmaceutical or veterinary applications is one particularly useful area for which compositions of the invention find utility.

The invention will now be further illustrated by the following Examples, which are not to be construed as limiting the scope of the invention. All quantities given are parts by weight, unless otherwise stated.

EXAMPLE 1

A mixture of 5.0 parts of AQUALOSE W20 (20mol. polyethylene glycol ether of lanolin alcohol (LANETH-20), ex Westbrook Lanolin Company) is mixed mechanically with 25.0 parts of MEDILAN (Medical Grade Lanolin (anhydrous), ex Westbrook Lanolin Company), 1.0 part of BIOPURE (Imidazolidinyl Urea, ex Nipa Laboratories) and deionised water, 69.0 parts. The mixture is co-emulsified by 2 passes through a Microfluidics Microfluidiser (Model 110 F) at 55° C. and a pressure of 15,000 psi.

The emulsion produced had a low kinematic viscosity of 4.90 $mm^2sec^{-1}$ at 21° C. (measured using a glass U-tube viscometer as described in the British Pharmacopoeia, 1993 Edition (Appendix VII Method 1, carried out in accordance with ISO 3104, 1976)). It was found to be physically stable upon storage at 40° C. for at least 2 months and to 7 freeze-thaw cycles (−18/+20° C.). It was further observed to be physically stable after storage at room temperature for 11 months.

Examination of the droplet size and structure by established techniques (using a Malvern Mastersizer particle size measuring instrument, and freeze fracture followed by electron microscopy, respectively) showed that the emulsion may possibly be of a liposomal form, exhibiting a unilamellar structure. The median particle size was approximately 0.68 μm (range approximately 0.05 to 1.2 μm).

EXAMPLE 2

A mixture of 5.0 parts of AQUALOSE L30 (30 mol. polyethylene glycol ether of lanolin (PEG-30 LANOLIN), ex Westbrook Lanolin Company) is mixed mechanically with 25.0 parts of MEDILAN (Medical Grade Lanolin (anhydrous), ex Westbrook Lanolin Company), and Saline Solution 70.0 parts. The mixture is co-emulsified by 4 passes through a Microfluidics Microfluidiser (Model 110 F) at 55° C. and a pressure of 15,000 psi.

The emulsion formed had a low kinematic viscosity of 7.60 $mm^2sec^{-1}$ at 21° C. (measured in the same manner as in Example 1) and was found to be physically stable upon storage at 40° C. for at least 2 months and to 7 freeze-thaw cycles (−18/+20° C.). It was further observed to be physically stable after storage at room temperature for 8 months.

The physical structure of the droplets dispersed in the composition was found to be closely similar to that of the composition of Example 1, with the median dispersed droplet particle size being 0.93 μm.

EXAMPLE 3

Using the same preparative procedure as in Example 2, a composition was prepared according to the following formulation:

| Ingredient | Parts by weight |
| --- | --- |
| AQUALOSE W20 | 15 |
| MEDILAN | 15 |
| BIOPURE | 1 |
| Water (deionised) | 69 |

The composition was observed to be physically stable after storage for 4 weeks at 40° C.

EXAMPLE 4

Using the same preparative procedure as in Example 2, a composition was prepared according to the following formulation:

| Ingredient | Parts by weight |
| --- | --- |
| AQUALOSE W20 | 10 |
| MEDILAN | 20 |
| BIOPURE | 1 |
| Water (deionised) | 69 |

The composition was observed to be physically stable after storage for 4 weeks at 40° C. and furthermore substantially physically stable after 12 months at the same temperature. It was also observed to be physically stable after storage for 12 months at room temperature.

EXAMPLE 5

Using the same preparative procedure as in Example 2, a composition was prepared according to the following formulation:

| Ingredient | Parts by weight |
| --- | --- |
| AQUALOSE W20 | 2 |
| MEDILAN | 28 |
| BIOPURE | 1 |
| Water (deionised) | 69 |

The composition was observed to be physically stable after storage for 4 weeks at 40° C. It was also observed to be physically stable after storage for 12 months at room temperature.

The composition was found to have a median dispersed droplet particle size of 0.63 μm.

EXAMPLE 6

Using the same preparative procedure as in Example 2, a composition was prepared according to the following formulation:

| Ingredient | Parts by weight |
|---|---|
| AQUALOSE W20 | 8.33 |
| MEDILAN | 41.67 |
| BIOPURE | 1.00 |
| Water (deionised) | 49.00 |

The composition was observed to be physically stable after storage for 12 months at 40° C. It was also observed to be physically stable after storage for 12 months at room temperature.

EXAMPLE 7

Using the same preparative procedure as in Example 2, a composition was prepared according to the following formulation:

| Ingredient | Parts by weight |
|---|---|
| AQUALOSE W20 | 2.50 |
| MEDILAN | 12.50 |
| BIOPURE | 1.00 |
| Water (deionised) | 84.00 |

The composition was observed to be physically stable after storage for 12 months at 40° C. It was also observed to be physically stable after storage for 12 months at room temperature.

EXAMPLE 8

Example 7 was repeated, but without the BIOPURE and using 85.00 parts deionised water instead.

The same stability results were observed and the median dispersed droplet particle size in the composition was found to be 0.57 $\mu$m.

EXAMPLE 9

Using the same preparative procedure as in Example 2, a composition was prepared according to the following formulation:

| Ingredient | Parts by weight |
|---|---|
| AQUALOSE W20 | 0.83 |
| MEDILAN | 4.17 |
| Water (deionised) | 95.00 |

The median dispersed droplet particle size in the composition was found to be 0.62 $\mu$m.

EXAMPLE 10

Using the same preparative procedure as in Example 2, a composition was prepared according to the following formulation:

| Ingredient | Parts by weight |
|---|---|
| AQUALOSE W20 | 0.33 |
| MEDILAN | 1.67 |
| Water (deionised) | 98.00 |

The median dispersed droplet particle size in the composition was found to be 0.62 $\mu$m.

EXAMPLE 11

Using the same preparative procedure as in Example 2, a composition was prepared according to the following formulation:

| Ingredient | Parts by weight |
|---|---|
| AQUALOSE L75 | 5 |
| MEDILAN | 25 |
| BIOPURE | 1 |
| Water (deionised) | 69 |

The composition was observed to be physically stable after storage for 11 months at room temperature. The median dispersed droplet particle size was found to be 0.47 $\mu$m. After autoclaving a sample of the composition at 121° C. for 15 minutes the 11 month old sample was still observed to be physically stable. After autoclaving the median particle size was found to be 0.69 $\mu$m.

EXAMPLE 12

Using the same preparative procedure as in Example 2, a composition was prepared according to the following formulation:

| Ingredient | Parts by weight |
|---|---|
| AQUALOSE L75 | 5 |
| MEDILAN | 5 |
| BIOPURE | 1 |
| Water (deionised) | 89 |

The median dispersed droplet particle size was found to be 0.56 $\mu$m.

EXAMPLE 13

Using the same preparative procedure as in Example 2, a composition was prepared according to the following formulation:

| Ingredient | Parts by weight |
|---|---|
| AQUALOSE LL100 | 5 |
| MEDILAN | 5 |
| BIOPURE | 1 |
| Water (deionised) | 89 |

The composition was observed to be physically stable for up to about 48 hours.

EXAMPLE 14

Using the same preparative procedure as in Example 2, a composition was prepared according to the following formulation:

| Ingredient | Parts by weight |
|---|---|
| AQUALOSE W20 | 5 |
| White soft paraffin | 25 |
| BIOPURE | 1 |
| Water (deionised) | 69 |

The composition was observed to be physically stable after storage for 11 months at room temperature. The median dispersed droplet particle size was found to be 0.66 $\mu$m. After autoclaving a sample of the composition at 121° C. for 15 minutes the 11 month old sample was still observed to be physically stable. After autoclaving the median particle size was found to be 0.61 $\mu$m.

EXAMPLE 15

Using the same preparative procedure as in Example 2, a composition was prepared according to the following formulation:

| Ingredient | Parts by weight |
|---|---|
| AQUALOSE W20 | 5 |
| White soft paraffin | 12.5 |
| Heavy liquid paraffin | 12.5 |
| BIOPURE | 1 |
| Water (deionised) | 69 |

The composition was observed to be physically stable after storage for 11 months at room temperature. The median dispersed droplet particle size was found to be 0.56 $\mu$m. After autoclaving a sample of the composition at 121° C. for 15 minutes the 11 month old sample was still observed to be physically stable. After autoclaving the median particle size was found to be 1.62 $\mu$m.

EXAMPLE 16

Using the same preparative procedure as in Example 2, a composition was prepared according to the following formulation:

| Ingredient | Parts by weight |
|---|---|
| AQUALOSE W20 | 5 |
| Heavy liquid paraffin | 25 |
| BIOPURE | 1 |
| Water (deionised) | 69 |

The composition was observed to be physically stable after storage for 11 months at room temperature. The median dispersed droplet particle size was found to be 0.44 $\mu$m. After autoclaving a sample of the composition at 121° C. for 15 minutes the 11 month old sample was still observed to be physically stable. After autoclaving the median particle size was found to be 0.46 $\mu$m.

EXAMPLE 17

Using the same preparative procedure as in Example 2, a composition was prepared according to the following formulation:

| Ingredient | Parts by weight |
|---|---|
| AQUALOSE W20 | 2 |
| MEDILAN OIL[1] | 28 |
| BIOPURE | 1 |
| Water (deionised) | 69 |

[1] ex Westbrook Lanolin Company

The composition was observed to be physically stable after storage for 8 months at room temperature.

EXAMPLE 18

Using the same preparative procedure as in Example 2, composition was prepared according to the following formulation:

| Ingredient | Parts by weight |
|---|---|
| AQUALOSE W20 | 5 |
| MEDILAN | 20 |
| MEDILAN OIL | 5 |
| BIOPURE | 1 |
| Water (deionised) | 69 |

The composition was observed to be physically stable after storage for 11 months at room temperature.

EXAMPLE 19

Using the same preparative procedure as in Example 2, a composition was prepared according to the following formulation:

| Ingredient | Parts by weight |
|---|---|
| AQUALOSE W20 | 5 |
| MEDILAN | 20 |
| LANESTA S[1] | 5 |
| BIOPURE | 1 |
| Water (deionised) | 69 |

[1] Isoproyl lanolate, ex Westbrook Lanolin Company

The composition was observed to be physically stable after storage for 11 months at room temperature.

The median dispersed droplet particle size in the composition was found to be 0.55 $\mu$m.

EXAMPLE 20

Using the same preparative procedure as in Example 2, a composition was prepared according to the following formulation:

| Ingredient | Parts by weight |
| --- | --- |
| AQUALOSE W20 | 5 |
| MEDILAN | 20 |
| Isopropyl palmitate[1] | 5 |
| BIOPURE | 1 |
| Water (deionised) | 69 |

[1]ex Unichema

The composition was observed to be physically stable after storage for 11 months at room temperature.

The median dispersed droplet particle size in the composition was found to be 0.58 μm.

EXAMPLE 21

Using the same preparative procedure as in Example 2, a composition was prepared according to the following formulation:

| Ingredient | Parts by weight |
| --- | --- |
| AQUALOSE W20 | 5 |
| MEDILAN | 20 |
| Heavy liquid paraffin | 5 |
| BIOPURE | 1 |
| Water (deionised) | 69 |

The composition was observed to be physically stable after storage for 11 months at room temperature.

The median dispersed droplet particle size in the composition was found to be 0.56 μm.

EXAMPLE 22

Using the same preparative procedure as in Example 2, a composition was prepared according to the following formulation:

| Ingredient | Parts by weight |
| --- | --- |
| AQUALOSE W20 | 5 |
| MEDILAN | 20 |
| Dimethicone[1] | 5 |
| BIOPURE | 1 |
| Water (deionised) | 69 |

[1]350cS, ex Basildon Chemicals

The composition was observed to be physically stable after storage for 8 months at room temperature.

The median dispersed droplet particle size in the composition was found to be 0.53 μm.

EXAMPLE 23

Example 1 was repeated, but using an emulsification pressure of 10,000 psi.

The resulting composition was observed to be physically stable for 4 weeks at 40° C., for 12 months at room temperature, and furthermore was observed to be substantially physically stable after 12 months at 40° C.

EXAMPLE 24

Example 1 was repeated, but using an emulsification pressure of 5,000 psi.

The resulting composition was observed to be physically stable for 4 weeks at 40° C. and for 12 months at room temperature.

EXAMPLE 25

Example 1 was repeated, but using an emulsification temperature of 40° C.

The resulting composition was observed to be physically stable for 4 weeks at 40° C.

EXAMPLE 26

Example 1 was repeated, again using an emulsification temperature of 55° C.

The resulting composition was observed to be physically stable for 4 weeks at 40° C., for 12 months at room temperature, and furthermore was observed to be substantially physically stable after 12 months at 40° C.

EXAMPLE 27

Example 1 was repeated, but using an emulsification temperature of 70° C.

The resulting composition was observed to be physically stable for 4 weeks at 40° C., for 12 months at room temperature, and furthermore was observed to be substantially physically stable after 12 months at 40° C.

EXAMPLE 28

Using the same preparative procedure as in Example 1, a composition was prepared according to the following formulation:

| Ingredient | Parts by weight |
| --- | --- |
| AQUALOSE W20 | 5 |
| MEDILAN | 25 |
| Hydrogen peroxide (35% w/w) | 1 |
| Water (deionised) | 69 |

The composition was observed to be physically stable after storage for 8 months at room temperature.

EXAMPLE 29

Using the same preparative procedure as in Example 1, a composition was prepared according to the following formulation:

| Ingredient | Parts by weight |
| --- | --- |
| AQUALOSE W20 | 5 |
| MEDILAN | 25 |
| ARGOQUAT[1] | 1 |
| Water (deionised) | 69 |

[1]Quaternium-33/dipropylene glycol (1:1), ex Westbrook Lanolin Company.

The composition was observed to be physically stable after storage for 6 months at room temperature.

The median dispersed droplet particle size in the composition was found to be 0.72 μm.

EXAMPLE 30

Using the same preparative procedure as in Example 2, a composition was prepared according to the following formulation:

| Ingredient | Parts by weight |
| --- | --- |
| AQUALOSE W20 | 5 |
| Isopropyl palmitate[1] | 25 |
| BIOPURE | 1 |
| Water (deionised) | 69 |

[1] ex Unichema

The composition was observed to be physically stable after storage for 4 weeks at room temperature.

EXAMPLE 31

This example illustrates the utility of the composition of Example 1 (but excluding the BIOPURE preservative) for transdermal drug delivery.

Ninety-five parts of the emulsion exemplified in Example 1 (but prepared without the BIOPURE preservative) is mixed with five parts (by weight) of Ibuprofen (ex. Sigma, Gillingham, Dorset, UK) using a Teflon coated magnetic stirrer bar at room temperature for 24 hours.

Two hundred microliters of the emulsion/Ibuprofen mixture is transferred to the uppermost surface of a section of isolated human stratum corneum (female breast, prepared by heat stripping at 65° C. in accordance with the dry heat method described in Methods in Skin Research, Eds. D. Skerrow and C.J. Skerrow, J. Wiley, 1985, pp. 615–616), placed over the receptor chamber of a glass Franz cell. Receptor fluid (volume 4.2–4.5 ml) is 10% ethanol/0.1 M phosphate buffered saline, pH 7.36. The cell is placed in a jacketed enclosure at 32° C. and stirred magnetically. Samples (500 microliters) are removed through a side arm at timed intervals and assayed for their Ibuprofen content by HPLC. The amount of the drug delivered through the stratum corneum is calculated by reference to standard amounts of Ibuprofen and compared with other formulations using the same donor skin. The flux (J) in microgrammes of Ibuprofen/sq. cm of skin/hour is calculated for each test and reference mixture.

The results are shown in Table 1 below.

TABLE 1

IBUPROFEN SKIN FLUX

| FORMULATION | FLUX $\mu g/cm^2/hr$ | Cumulative amounts Ibuprofen after 24 hours ($\mu g/cm^2$) |
| --- | --- | --- |
| 1) Lanolin/liposomal micro emulsion + Ibuprofen (5%) of Example 3 | 18.3<br>19.9 (mean 20.7)<br>23.8 | 439<br>477<br>570 |
| 2. Cetyl Acetate | 14.8 | 338 |
| 3. Commercial gel based on propylene glycol/ethanol formulation + 5% Ibuprofen ("Ibuleve R" (trade mark)) | 44.5 (mean 45.8)<br>47.0 | 1067<br>1129 |

EXAMPLE 32

The procedure of Example 3 was repeated to test the utility of the same composition for the transdermal delivery of testosterone, which replaced the Ibuprofen in Example 3 but was incorporated in the same amount.

The results are shown in Table 2 below.

TABLE 2

TESTOSTERONE SKIN FLUX

| FORMULATION | FLUX $\mu g/cm^2/hr$ | Cumulative delivery at Testosterone ($\mu g/cm^2/24$ hrs) |
| --- | --- | --- |
| 1) Lanolin/liposomal micro emulsion + Testosterone (5%) of Example 4 | 0.44 | 10.5 |

EXAMPLES 33 to 37

To demonstrate the efficacy of compositions according to the invention for delivering a variety of other pharmaceutical actives, the procedure of Example 31 was repeated, but using various alternative active materials. The level of active incorporated (weight of active per ml of the composition of the invention) and the resulting transdermal delivery thereof are set out in Table 3 below.

TABLE 3

| Example | Active | Amount incorporated (mg/ml) | Cumulative amount delivered ($\mu g/cm^2/24$ hr) |
| --- | --- | --- | --- |
| 33 | Verapimil hydrochloride | 50 | 44 |
| 34 | Metronidazole | 5 | 27.9 |
| 35 | 5-Fluorouracil | 25 | 13.6 |
| 36 | Fentanyl citrate | 5 | 9.0 |
| 37 | Vincristine sulphate | 5 | 36.8 |

What is claimed is:

1. An aqueous composition comprising, in addition to water:
   (a) one or more surfactant materials selected from polyoxyalkylene condensate derivatives of lanolin or a lanolin derivative; and
   (b) a lipid component comprising one or more lipid materials selected from the group consisting of lanolin, lanolin derivatives and $C_{2-60}$ hydrocarbons, the lipid materials being present as particles emulsified by the one or more lanolin-derived surfactant materials and having a median particle size of less than about 5 microns.

2. A composition according to claim 1, wherein the lipid component comprises one or more lipid materials selected from the group consisting of lanolin and one or more lanolin derivatives.

3. A composition according to claim 2, wherein the lanolin and lanolin derivatives are selected from the group consisting of wool wax, purified lanolin, lanolin oil, lanolin alcohols and lanolin esters.

4. A composition according to claim 1, wherein the median particle size of the lipid component is in the range of from 0.01 to 1 $\mu m$.

5. A composition according to claim 1 wherein the composition has a kinematic viscosity in the range of from 1.5 to 20 $mm^2sec^{-1}$ at 21° C.

6. A composition according to claim 1, wherein the amount of the lipid component in the composition is the range of from 0.1 to 60% by weight.

7. A composition according to claim 1, wherein the polyoxyalkylene condensate derivative of lanolin or a lanolin derivative is selected from the group consisting of one or more polyethyleneglycol ethers of lanolin alcohol, one or more polypropyleneglycol ethers of lanolin alcohol, one or more polyethyleneglycol ethers of lanolin, and one or more PPG/PEG ethers of lanolin oil, and mixtures thereof.

8. A composition according to claim 1, further comprising one or more co-surfactant materials selected from naturally-derived surfactants which act as matrix- or film-formers, and synthetic surfactants selected from anionic, nonionic, cationic, zwitterionic and amphoteric surfactants, or mixtures thereof.

9. A composition according to claim 1, wherein the surfactant component of the composition consists substantially only of the one or more polyoxyalkylene condensate derivatives of lanolin or a derivative thereof, with other surfactant materials being substantially absent.

10. A composition according to claim 1, wherein the total amount of surfactant in the composition is in the range of from 0.1 to 25% by weight.

11. A composition according to claim 2,
wherein the lipid component comprises medical grade lanolin (anhydrous).

12. A composition according to claim 1,
wherein the surfactant materials are selected from the group consisting of the polyethylene glycol ether of lanolin alcohol (laneth 20) and ethoxylated medical grade lanolin (anhydrous).

13. A pharmaceutical, dermatological or cosmetic composition comprising a pharmaceutically, dermatologically or cosmetically active agent together with a carrier therefore, in which the carrier comprises an aqueous composition comprising, in addition to water:
  (a) one or more surfactant materials selected from polyoxyalkylene condensate derivatives of lanolin or a lanolin derivative; and
  (b) a lipid component comprising one or more lipid materials selected from the group consisting of lanolin, lanolin derivatives and $C_{12-60}$ hydrocarbons, the lipid materials being present as particles emulsified by the one or more lanolin-derived surfactant materials and having a median particle size of less than about 5 microns.

14. A method for treatment or prevention of a condition of a mammal, which the method comprises topically applying to the mammal in need thereof a composition according to claim 13.

15. A method according to claim 14,
wherein the condition is selected from the group consisting of traumatized skin, eczema, psoriasis, dry and damaged skin and hair, and for potential skin infections.

* * * * *

UNITED STATES PATENT AND TRADEMARK OFFICE
CERTIFICATE OF CORRECTION

PATENT NO. : 6,224,853 B1
DATED : May 1, 2001
INVENTOR(S) : Steel et al.

It is certified that error appears in the above-identified patent and that said Letters Patent is hereby corrected as shown below:

Column 1,
Line 53, after "Bottari," delete "20"

Column 12,
Line 23, after "Example 2," and insert therefor -- a --

Column 16,
Line 18, after "demonstrate" delete "the-efficacy" and insert therefor -- the efficacy --
Line 24, after "resulting" insert therefor -- observed. --
Line 46, after "and" delete "$C_{2-60}$" and insert therefor -- $C_{12-60}$ --

Column 17,
Line 9, after "from" insert therefor -- the group consisting of --
Line 17, before "of" delete "derivatives" and insert therefor -- derivative(s) --

Signed and Sealed this

Eleventh Day of January, 2005

JON W. DUDAS
*Director of the United States Patent and Trademark Office*